United States Patent [19]

Portney et al.

[11] Patent Number: 5,061,840

[45] Date of Patent: Oct. 29, 1991

[54] MANUFACTURE OF OPHTHALMIC LENSES BY EXCIMER LASER

[75] Inventors: Valdemar Portney, Irvine; Albert C. Ting, Laguna Niguel; Timothy R. Willis, El Toro, all of Calif.

[73] Assignee: Allergan, Inc., Irvine, Calif.

[21] Appl. No.: 496,104

[22] Filed: Mar. 16, 1990

Related U.S. Application Data

[60] Continuation of Ser. No. 217,275, Feb. 28, 1989, abandoned, which is a division of Ser. No. 919,206, Oct. 14, 1986, Pat. No. 4,842,782.

[51] Int. Cl.$^5$ .............................................. B33K 26/00
[52] U.S. Cl. .............................. 219/121.68; 156/643; 219/121.73; 219/121.75
[58] Field of Search ...................... 219/121.68, 121.69, 219/121.73, 121.75; 156/643

[56] References Cited

U.S. PATENT DOCUMENTS

| | | | |
|---|---|---|---|
| 3,410,203 | 11/1968 | Fischbeck | 101/1 |
| 3,440,388 | 4/1969 | Otstot et al. | 219/65 |
| 3,549,733 | 12/1970 | Caddell | 219/121.69 X |
| 3,657,085 | 4/1972 | Hoffmeister et al. | 204/157.1 R |
| 3,742,182 | 6/1973 | Saunders | 219/121.85 |
| 3,972,599 | 8/1976 | Engel et al. | 219/121.6 X |
| 4,032,861 | 6/1977 | Rothrock | 219/121.6 |
| 4,081,655 | 3/1978 | Gale | 214/121.85 |
| 4,108,659 | 8/1978 | Dini | 346/76 L |
| 4,128,752 | 12/1978 | Gravel | 219/121.68 |
| 4,147,402 | 4/1979 | Chown | 350/96.18 |
| 4,156,124 | 5/1979 | Macken et al. | 219/121.6 |
| 4,194,814 | 3/1980 | Fischer et al. | 351/160 R |
| 4,219,721 | 8/1980 | Kamen et al. | 219/121.85 |
| 4,275,288 | 6/1981 | Makosch et al. | 219/121.75 |
| 4,307,046 | 12/1981 | Neefe | 264/1.4 |
| 4,323,317 | 4/1982 | Hasegawa | 219/121.75 X |
| 4,370,175 | 1/1983 | Levatter | 219/121.6 X |
| 4,402,579 | 9/1983 | Poler | 351/160 R |
| 4,414,059 | 11/1983 | Blum et al. | 156/659.1 |
| 4,430,548 | 2/1984 | Macken | 219/121.67 |
| 4,450,593 | 5/1984 | Poler | 351/160 R |
| 4,455,893 | 6/1984 | Astero | 76/107 R |
| 4,473,735 | 9/1984 | Steffen | 219/121.66 |
| 4,510,005 | 4/1985 | Nijman | 156/221 |
| 4,556,524 | 12/1985 | Cullis et al. | 264/1.2 |
| 4,563,565 | 1/1986 | Kampfer et al. | 219/121.69 |
| 4,642,439 | 2/1987 | Miller et al. | 219/121.72 |
| 4,644,130 | 2/1987 | Bachmann | 219/121.69 |
| 4,652,721 | 3/1987 | Miller et al. | 219/121.67 |
| 4,665,913 | 5/1987 | L'Esperance, Jr. | 128/303.1 |
| 4,669,466 | 6/1987 | L'Esperance | 128/303.1 |
| 4,718,418 | 1/1988 | L'Esperance, Jr. | 128/303.1 |
| 4,721,379 | 1/1988 | L'Esperance, Jr. | 128/303.1 X |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |

FOREIGN PATENT DOCUMENTS

| | | |
|---|---|---|
| 1038935 | 9/1978 | Canada ............................ 219/121.78 |
| 2546692 | 4/1977 | Fed. Rep. of Germany . |
| 2510768 | 7/1982 | France . |
| 29627 | 2/1983 | Japan . |
| 97787 | 6/1984 | Japan . |

OTHER PUBLICATIONS

"Laser Applications in Semiconductor Microlithography"; Kanti Jain; Lasers & Applications; Sep. 1983, pp. 49-56.

"Effective Deep Ultraviolet Photoetching of Polymethyl Methacrylate by an Excimer Laser"; Y. Kawamura, K. Toyoda and S. Namba; Appl. Phys. Lett. 40(5), 1 Mar. 1982; pp. 374-375.

"Deep-Ultraviolet Spatial-Period Division Using an Excimer Laser"; A. M. Hawryluk and Henry I. Smith; Optic Letters; vol. 7, No. 9, Sep. 1983; pp. 402-404.

(List continued on next page.)

*Primary Examiner*—C. L. Albritton
*Attorney, Agent, or Firm*—Gordon L. Peterson

[57] ABSTRACT

Complex small objects such as ophthalmic lenses are quickly and accurately fabricated from plastic or glass blanks of ablatable material such as plastic or glass by cutting, shaping, and radiusing the blank entirely by laser light, using appropriate masks and focusing optics.

31 Claims, 2 Drawing Sheets

OTHER PUBLICATIONS

"Laser Ablation of Organic Polymers: Microscopic Models for Photochemical and Thermal Processes"; B. Garrison et al., Journal of Applied Physics, 57(8); Apr. 15, 1985; pp. 2909-2914.

"Kinetics of the Ablative Photodecomposition of Organic Polymers in the Far-Ultraviolet (193 nm)"; IBM Thomas J. Watson Research Center; pp. 1-11.

"Action of Far-Ultraviolet Light on Organic Polymer Films: Applications to Semiconductor Technology", IBM Thomas J. Watson Research Center; pp. 1-9.

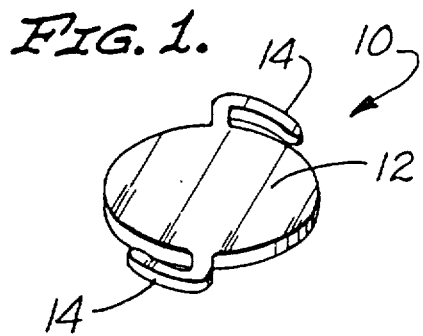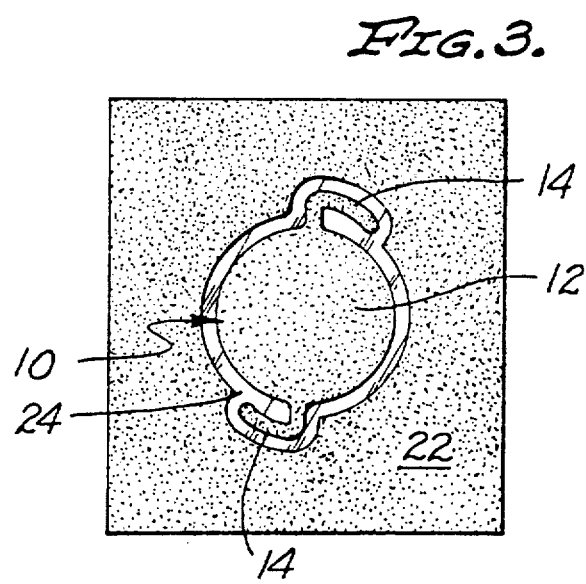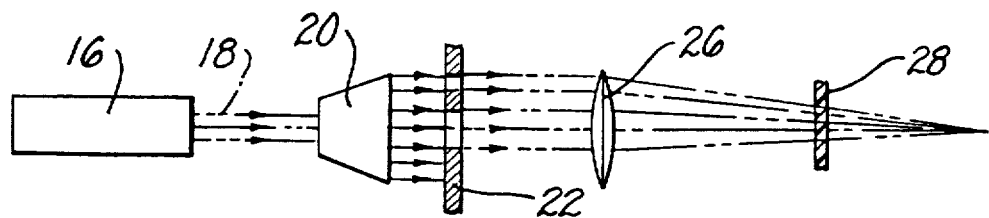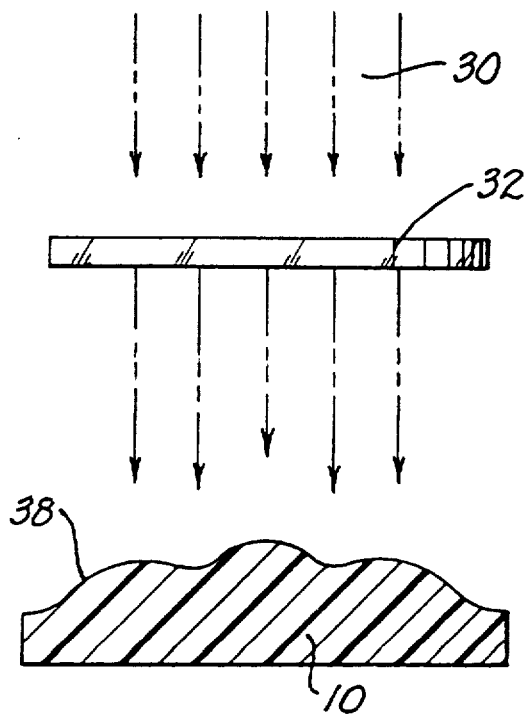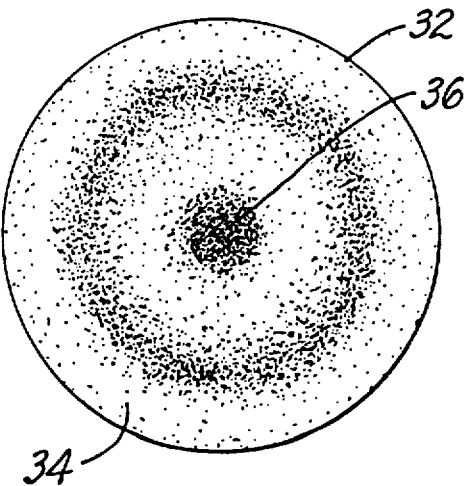

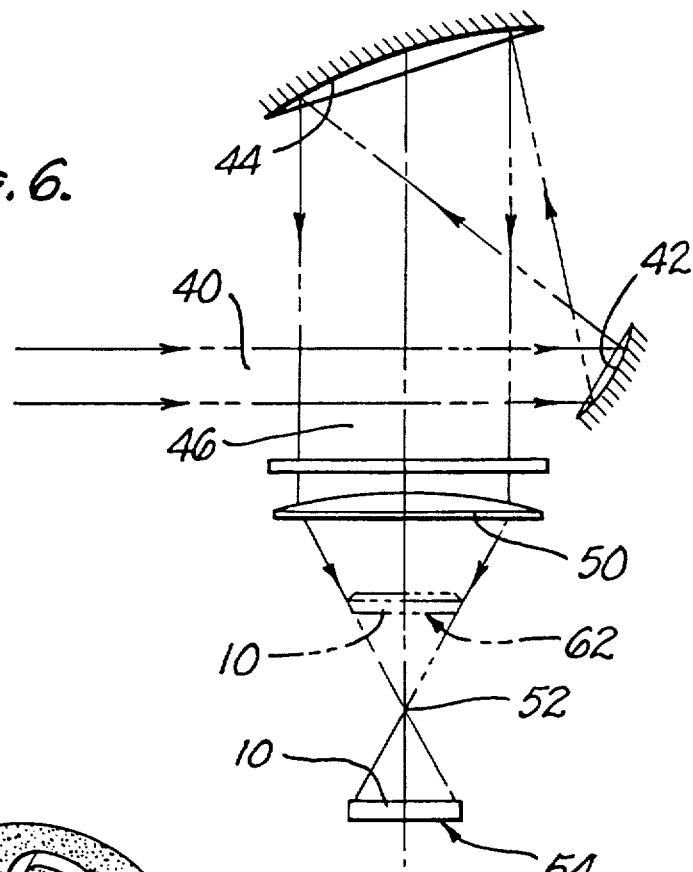
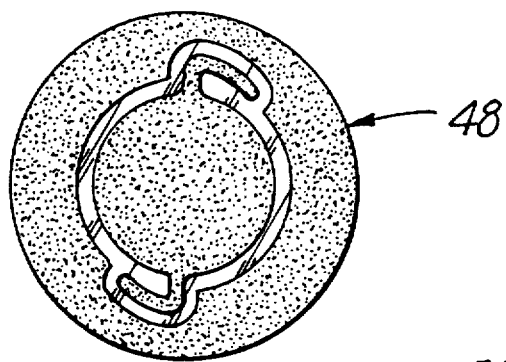
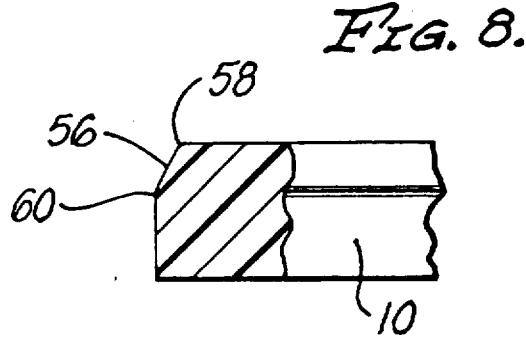
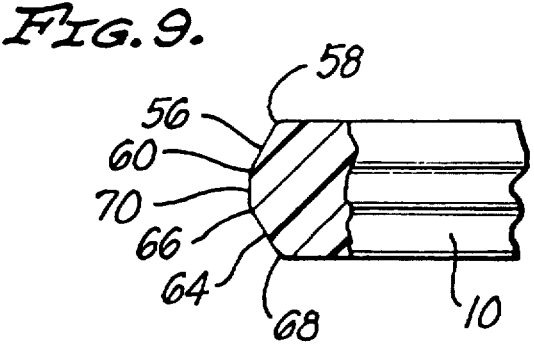

MANUFACTURE OF OPHTHALMIC LENSES BY EXCIMER LASER

This application is a continuation of application Ser. No. 217,275 filed Feb. 28, 1989 now abandoned and also entitled "MANUFACTURE OF OPHTHALMIC LENSES BY EXCIMER LEASER", which is a division of application Ser. No. 919,206 filed Oct. 14, 1986 now U.S. Pat. No. 4,842,782 which issued Jun. 27, 1989.

FIELD OF THE INVENTION

This invention relates to the manufacture of ophthalmic lenses such as a contact, corneal implant, and intramic ocular lenses, or of other small plastic or glass objects of similar shape, and more particularly to a method of making such lenses or objects with a high degree of precision at low cost by using an excimer laser.

BACKGROUND OF THE INVENTION

Ophthalmic lenses are normally manufactured by a mechanical process in which a block of polymethylmethacrylate (PMMA) is machined while being adhesively held on a support. The machining is quite difficult because of the small size of the lens and the intricacy of the shape into which the lens must be machined.

Typically, three operations must be performed to shape a lens:

1) the workpiece must be cut out from a blank to form, e.g., an integral optic and haptic;
2) the surface of the workpiece must be machined to the desired optical specifications (which may include convexities or concavities of varying radii at different points on the surface of the lens; and
3) the edges of the workpiece must be radiused or rounded.

In the prior art, the edge rounding step alone typically required 7-14 days of gemstone tumbling, and precision was hard to accomplish in all of the steps.

SUMMARY OF THE INVENTION

The present invention provides a method of fabricating ophthalmic lenses or similar small objects quickly and accurately by using a laser, and particularly an excimer laser, to cut, surface-model and bevel a workpiece which is preferably made of PMMA but may, for appropriate purposes, be made of other plastics or of glass. The type and tuning of the laser is dependent upon the material of the blank.

In accordance with the invention, the workpiece is first cut to shape by shining a laser beam through a mask outlining the form of the cut required to shape (in the case of an ophthalmic lens) the optic and haptic. Considerable precision can be obtained in this step by expanding the laser beam in front of the mask and then reducing it beyond the mask to provide fine detail from a relatively large mask. The depth of the cut can be controlled by the number and energy of the pulses.

The surface modeling of the lens is next achieved by masking a laser beam in such a way that its energy distribution varies across the surface of the workpiece so as to ablate it to differing degrees at different points of the surface. This can be achieved by using a mask of varying opacity or a semi-transparent mirror with a coating of varying thickness at different points on the surface. This step, if desired, may be performed before the cutting step.

Finally, a laser beam is masked and focused generally into the form of a hollow cone whose tip is the focal point of the beam. By exposing the workpiece to the beam on one side of the focal point and then on the other, two bevel cuts are made along the perimeter of the upper and lower surfaces, respectively, of the workpiece. When combined with a vertical section of the side of the workpiece, these bevel cuts form an approximation of a rounded edge which is further softened by the slight melting of the workpiece material produced by the heat generated by the laser during cutting.

It is therefore the object of the invention to quickly and accurately produce a complex small object such as an ophthalmic lens from a blank entirely by the use of a laser.

BRIEF DESCRIPTION OF THE DRAWINGS

FIG. 1 is a perspective view of an intraocular lens to be manufactured by the method of this invention;

FIG. 2 is a schematic diagram of a laser optic used in the cutting step of the invention;

FIG. 3 is a plan view of the mask used in the cutting step;

FIG. 4 is a schematic diagram illustrating the surface modeling step of this invention;

FIG. 5 is a plan view of the mask used in the surface modeling step;

FIG. 6 is a schematic diagram illustrating the edge beveling step of this invention;

FIG. 7 is a plan view of the mask used in the beveling step;

FIG. 8 is a fragmentary detail section of the workpiece after the first beveling step; and FIG. 9 is a fragmentary detail section of the workpiece after the second beveling step.

DESCRIPTION OF THE PREFERRED EMBODIMENT

In the preferred embodiment of the invention, which is the manufacture of ophthalmic lenses from a PMMA blank, the method of this invention is carried out with an excimer laser, i.e. a laser operating in the high ultraviolet wavelengths. An argon-fluoride laser operating at a wavelength of 193 nm in 250 millijoule pulses is preferred, but broadly any ultraviolet wavelength substantially absorbed by the material of the workpiece may be used. The choice of the laser is dictated by its ability to break up the large molecules of the workpiece material (as in the case of plastic) or to melt the material (as in the case of glass) so that the material will ablate.

FIG. 1 shows a typical intraocular lens which may be produced by the method of this invention. The workpiece 10 has an optic 12 which forms the actual lens, and a haptic 14 by which the lens is anchored in the patient's eye. In the prior art, polypropylene is usually used for the haptic 14, and PMMA is used for the optic 12. However, both the optic 12 and the haptic 14 may be formed of PMMA, and in the process of this invention this is preferable because the entire workpiece can be cut as a single piece. Of course, other ultraviolet-absorbing materials than PMMA (e.g. silicone) may be used for the workpiece if they are medically acceptable and properly ablatable.

FIG. 2 shows an arrangement useful in cutting the workpiece 10 from a block of PMMA. An excimer laser 16 emits a beam 18 of coherent ultraviolet light. Because the diameter of beam 18 is fairly small, a conventional laser beam expander 20 is used to expand the beam 18 to a diameter of several centimeters. The beam 18 is collimated between the beam expander 20 and the mask 22 (FIG. 2). A mask 22 best shown in FIG. 3 is formed integrally wi the beam expander 20 or placed into the path of the expanded beam 18 to allow only a narrow strip of light in the shape of the outline 24 of the workpiece 10 to pass through the mask 22.

A beam converger or focusing optic 26 is used to project a reduced image of the outline 24 onto the PMMA block 28. Repeated pulses of the laser 16 will ablate the material of the block 28 until the profiled lens or workpiece 10 is very precisely cut out of the block 28. The precision of the cut is enhanced (and the power density of the beam increased) by the use of a relatively large mask 22 and a substantial reduction of the mask image on the block 28.

After being cut out from the block 28, the workpiece 10 is placed into the path of an excimer laser beam 30 (FIG. 4) which has a uniform energy distribution across its area. A mask 32 is interposed between the workpiece 10 and beam 32.

As best shown in FIG. 5, the mask 32 has different degrees of transparency at different points on the mask 32. For example, the mask 32 may have a coating of variable transmission characteristics, or it may be a neutral density filter (such as a polarizing or haze filter) with non-uniform transmission characteristic. In any event, the mask 32 transmits a large amount of beam energy in the areas 34 corresponding to desired depressions in the workpiece 10, and a small amount in the areas 36 corresponding to desired protrusions in the workpiece 10.

By appropriately controlling the transmission characteristics of the mask 32, it is possible to model or shape the surface 38 of the workpiece 10 in any desired manner without complex machining, and to do so precisely in a small amount of time.

In an alternative embodiment of the invention, the mask 32 may take the form of a semi-transparent mirror with a reflective coating whose thickness varies along its surface. In that embodiment, the laser energy not used for ablation is reflected away from the workpiece.

After the shaping or modeling step of FIGS. 4 and 5, the workpiece is fully formed but has sharp vertical edges which are not suitable for intraocular use. In the prior art, the edges of the workpiece were radiused or rounded by gemstone tumbling for 7-14 days, but besides being time-consuming, this prior art method often defeated the carefully achieved precision of the workpiece.

In accordance with the invention, an excimer laser beam 40 (FIG. 6) is expanded by a beam expander or (preferably) by a pair of curved mirrors 42, 44. The use of reflective rather than refractive beam expanding optics is preferred because it permits higher power transfer with smaller optics while avoiding damage to the optics.

The expanded beam 46 is conducted through a mask 48 best shown in FIG. 7 to a focusing lens 50. As a result, a beam generally in the form of a hollow cone is produced, with the tip of the cone being the focal point 52.

In order to round its edges, the workpiece 10 is first positioned below the focal point 52 at 54, and the laser is turned on. The conical shape of the beam will produce a bevel 56 (FIG. 8) on the edges of the workpiece 10. The ends of the bevel 56 are slightly rounded at 58, 60 by the small amount of heat which is produced during the ablation of workpiece material which forms the bevel 56.

When the bevel 56 has been fully formed, the workpiece 10 is positioned above the focal point 52 at 62, and the beam is turned on again. This time, the conical shape of the beam results in cutting a bevel 64 (FIG. 9) whose edges are slightly rounded at 66, 68 for the same reason as described above.

When combined with the vertical surface 70, the bevels 56, 64 and their rounded extremities provide a sufficient approximation of a rounded edge for the workpiece 10 to make it suitable for implantation in a patient's eye without danger of irritation.

It will be seen that the above-described process provides a fast and accurate way of manufacturing intraocular lenses without the use of complex machining equipment. The invention can, of course, be carried out with variations: for example, a very narrow laser beam may be moved around the periphery of the workpiece in the cutting and beveling steps, rather than cutting or beveling the entire periphery at once; or a mask may be scanned rather than being exposed all at once.

We claim:

1. Apparatus for cutting a small object such as an ophthalmic lens from a blank of ablatable material, comprising:
    a) an excimer laser arranged to emit a beam of laser light;
    b) beam expansion means for expanding said beam;
    c) mask means interposed in said expanded beam for transmitting only portions of said beam in the outline of said object; and
    d) beam reducing means for projecting a reduced image of said outline onto said blank.

2. Apparatus for beveling the edges of a small object of ablatable material such as an ophthalmic lens, comprising;
    a) a beam of excimer laser light;
    b) a mask disposed in said beam, said mask having a central non-light-transmitting area in the shape of said object;
    c) optic means for focusing said beam as masked by said mask; and
    d) means for selectively positioning said object in said beam in a first position ahead of or a second position beyond the focal point of said optic means;
    e) said positions being positions in which the edges of the masked portion of said beam are substantially coincident with the edges of said object.

3. The apparatus of claim 2, in which said material is plastic.

4. The apparatus of claim 3, in which said material is polymethlmethacrylate.

5. The apparatus of claim 2, in which said material is glass.

6. An apparatus comprising:
    a mask;
    a laser for directing laser energy toward the mask with the laser energy being unfocused at the mask;
    the mask having a variable transmissivity or reflectivity characteristics to the laser energy to provide a first laser beam of variable energy across its width whereby directing the laser beam of variable energy against a surface of a workpiece for a sufficient time removes material from multiple locations on the surface of the workpiece in accordance with said characteristics with more of the material being removed at one of the locations than is removed at another of the locations;

the first laser beam being unfocused at the workpiece; and said characteristics shaping the surface of the workpiece into an ophthalmic lens.

7. An apparatus as defined in claim 6 wherein the laser is an excimer laser.

8. An apparatus as defined in claim 6 including means for cutting the workpiece from a blank by exposing the blank to laser energy in the outline of said workpiece.

9. An apparatus as defined in claim 6 including means for directing a second laser beam toward a blank in a pattern without focusing the second laser beam at the blank for a sufficient length of time to cut the workpiece from the blank.

10. An apparatus as defined in claim 9 wherein the means for directing the second laser beam toward the blank includes a second mask and means for directing the second laser beam through the second mask with the second laser beam passing through the second mask being in said pattern.

11. An apparatus as defined in claim 9 including means for beveling an edge of the workpiece by exposing it to laser energy.

12. An apparatus as defined in claim 11 including a third mask and means for directing laser energy toward the third mask to the workpiece without focusing the laser energy at the workpiece to bevel an edge of the workpiece.

13. An apparatus as defined in claim 6 including means for beveling an edge of the workpiece by exposing it to laser energy.

14. An apparatus as defined in claim 6 including a second mask and means for directing laser energy toward the second mask to the workpiece without focusing the laser energy at the workpiece to bevel an edge of the workpiece.

15. An apparatus for cutting a workpiece from an object, said apparatus comprising:
a mask having a pattern through which laser energy can pass, said pattern being in the outline of the workpiece; and
a laser for directing laser energy through the mask and toward the object with the laser energy passing through the mask being in said pattern and being unfocused at the mask and the object whereby the laser energy can cut the workpiece in the shape of said pattern from the object.

16. An apparatus as defined in claim 15 including means for beveling an edge of the workpiece by exposing it to laser energy.

17. An apparatus as defined in claim 2 including a second mask and means for directing laser energy toward the second mask to the workpiece without focusing the laser energy at the workpiece to bevel an edge of the workpiece.

18. An apparatus as defined in claim 2 wherein said pattern is generally in the shape of an intraocular lens.

19. An apparatus as defined in claim 2 including means between the mask and the object for focusing the laser energy at a location spaced from the mask and the object.

20. Apparatus for beveling the edges of an object of ablatable material comprising:
a laser for providing a beam of laser energy;
a mask disposed in said beam to provide a masked laser beam, said mask having a central non-laser energy-transmitting area in the shape of said object;
means for directing the masked beam toward a focus;
means for positioning said object in said masked beam in a position spaced from said focus; and
the edge of the masked beam being substantially coincident with the edge of said object in said position.

21. An apparatus as defined in claim 20 wherein the laser energy is excimer laser energy.

22. An apparatus for cutting a workpiece from an object, said apparatus comprising:
a mask having a pattern through which laser energy can pass, said pattern being in the outline of the workpiece;
a laser for providing laser energy; and
means for directing the laser energy through the mask to the object with the laser energy entering the mask being collimated and with the laser energy being unfocused at the workpiece whereby the laser energy can cut the workpiece in the shape of said pattern from the object.

23. An apparatus as defined in claim 22 wherein the laser is an excimer laser.

24. An apparatus as defined in claim 22 wherein the directing means includes a beam expander between the laser and the mask and the laser energy between the beam expander and the mask is collimated.

25. An apparatus as defined in claim 22 wherein the directing means includes a beam expander between the laser and the mask and there are no lenses in the path of the laser energy between the beam expander and the mask.

26. An apparatus comprising:
a mask;
a laser for directing laser energy toward the mask with the laser energy being unfocused at the mask;
the mask having variable transmissivity or reflectivity characteristics to the laser energy to provide a laser beam of variable energy across its width whereby directing the laser beam of variable energy against a surface for a sufficient time removes material from multiple continuous locations on the surface in accordance with said characteristics with more of the material being removed at one of the locations than is removed at another of the locations; and
the laser beam being unfocused at the surface.

27. An apparatus as defined in claim 26 wherein the laser is an excimer laser.

28. An apparatus as defined in claim 26 wherein the mask has variable transmissivity characteristics.

29. An apparatus as defined in claim 26 wherein the mask has variable reflectivity characteristics.

30. An apparatus comprising:
a mask;
a laser for directing laser energy toward the mask with the laser energy being unfocused at the mask;
the mask having variable transmissivity or reflectivity characteristics to the laser energy to provide a laser beam of continuously variable energy across a portion of its width whereby directing the laser beam of variable energy against a surface for a sufficient time removes material from multiple locations on the surface in accordance with said characteristics to curve said surface; and
the laser beam being unfocused at the surface.

31. An apparatus comprising:

a mask;
a laser for directing laser energy toward the mask with the laser energy being unfocused at the mask;
the mask having variable transmissivity or reflectivity characteristics to the laser energy to provide a laser beam of variable energy across its width capable of shaping a surface into a lens surface whereby directing the laser beam of variable energy against the surface for a sufficient time removes material from multiple continuous locations on the surface in accordance with said characteristics to shape the surface into a lens surface; and
the laser beam being unfocused at the surface.

* * * * *

UNITED STATES PATENT AND TRADEMARK OFFICE
CERTIFICATE OF CORRECTION

PATENT NO.  : 5,061,840
DATED       : Oct. 29, 1991
INVENTOR(S) : Portney et al

It is certified that error appears in the above-identified patent and that said Letters Patent is hereby corrected as shown below:

Column 1, lines 14 and 15 change "intramic ocular" to --intraocular--.

Column 3, line 4 change "wi" to -- with --.

Column 3, line 59 change "7" to -- 6 --.

Column 4, line 61 before "variable" delete "a".

Column 5, line 27 change "11" to -- 10 --.

Column 5, line 55 change "2" to -- 15 --.

Column 5, line 60 change "2" to -- 15 --.

Column 5, line 62 change "2" to -- 15 --.

Column 6, line 43 change "continuous" to -- contiguous --.

Column 8, line 3 change "continuous" to -- contiguous --.

Signed and Sealed this

Twenty-fifth Day of May, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,061,840
DATED : October 29, 1991
INVENTOR(S) : Portney et al It is certified that error appears in the above-identified patent and that said Letters Patent is hereby corrected as shown below:

On title page, item [60] under "Related U.S. Application Data" change "217,275" to -- 317,275 --.

Signed and Sealed this

Sixteenth Day of May, 1995

Attest:

BRUCE LEHMAN

*Attesting Officer*    *Commissioner of Patents and Trademarks*